United States Patent
Maslow (10) Patent No.: US 11,116,926 B2
(45) Date of Patent: Sep. 14, 2021

(54) INTUBATING ENDOSCOPIC DEVICE

(71) Applicant: Andrew Maslow, Needham, MA (US)

(72) Inventor: Andrew Maslow, Needham, MA (US)

(*) Notice: Subject to any disclaimer, the term of this patent is extended or adjusted under 35 U.S.C. 154(b) by 333 days.

(21) Appl. No.: 15/717,351

(22) Filed: Sep. 27, 2017

(65) Prior Publication Data

US 2018/0085545 A1 Mar. 29, 2018

Related U.S. Application Data (60) Provisional application No. 62/400,340, filed on Sep. 27, 2016.

(51) Int. Cl.
| | |
|---|---|
| *A61M 16/04* | (2006.01) |
| *A61M 25/01* | (2006.01) |
| *A61B 1/005* | (2006.01) |
| *A61B 1/07* | (2006.01) |
| *A61B 1/04* | (2006.01) |
| *A61B 1/267* | (2006.01) |
| *A61B 1/015* | (2006.01) |

(52) U.S. Cl.
CPC ....... *A61M 16/0488* (2013.01); *A61B 1/0051* (2013.01); *A61B 1/0057* (2013.01); *A61B 1/015* (2013.01); *A61B 1/042* (2013.01); *A61B 1/07* (2013.01); *A61B 1/267* (2013.01); *A61B 1/2673* (2013.01); *A61M 25/0102* (2013.01); *A61B 1/0052* (2013.01); *A61M 16/0463* (2013.01); *A61M 16/0486* (2014.02); *A61M 2205/502* (2013.01); *A61M 2205/587* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,337,761 A | * | 7/1982 | Upsher | A61B 1/07 600/188 |
| 4,846,153 A | | 7/1989 | Berci | |
| 4,871,229 A | * | 10/1989 | Tashiro | A61B 1/00165 385/117 |
| 5,257,618 A | * | 11/1993 | Kondo | G02B 23/26 138/120 |

(Continued)

FOREIGN PATENT DOCUMENTS

WO WO-2017083648 A1 * 5/2017 ............. A61B 1/015

OTHER PUBLICATIONS

International Search Report and the Written Opinion of the International Searching Authority from corresponding PCT/US2017/053759 dated Nov. 30, 2017.

(Continued)

*Primary Examiner* — John P Leubecker
*Assistant Examiner* — Shankar Raj Ghimire
(74) *Attorney, Agent, or Firm* — Lando & Anastasi, LLP (57) ABSTRACT

An intubating device is provided for use with an endotracheal tube. In some embodiments, the intubating device includes a sheath having a distal end and a proximal end, and the sheath is configured to be introduced into a body cavity. The sheath has a rigid section, and the sheath has a flexible section at the distal end. The flexible section is selectively bendable. A control housing is located at the proximal end. The control housing includes a deflector for selectively bending the flexible section of the sheath.

20 Claims, 10 Drawing Sheets

(56) References Cited

U.S. PATENT DOCUMENTS

| | | | |
|---|---|---|---|
| 5,462,527 A * | 10/1995 | Stevens-Wright | A61B 18/1492 600/585 |
| 5,607,386 A | 3/1997 | Flam | |
| 5,665,052 A | 9/1997 | Bullard | |
| 5,733,242 A * | 3/1998 | Rayburn | A61B 1/0052 600/120 |
| 5,842,973 A * | 12/1998 | Bullard | A61M 16/0488 600/194 |
| 6,174,280 B1 * | 1/2001 | Oneda | A61B 1/00078 600/114 |
| 7,563,227 B2 | 7/2009 | Gardner | |
| 8,042,545 B2 | 10/2011 | Schwartz et al. | |
| 8,287,449 B2 | 10/2012 | Tanaka | |
| 2003/0069473 A1 * | 4/2003 | Barthel | A61B 1/0051 600/139 |
| 2004/0059191 A1 * | 3/2004 | Krupa | A61B 1/0052 600/146 |
| 2005/0075621 A1 * | 4/2005 | Rontal | A61B 17/22004 604/500 |
| 2006/0135961 A1 * | 6/2006 | Rosenman | A61M 25/0045 606/108 |
| 2006/0224103 A1 * | 10/2006 | Rontal | A61B 17/22 604/22 |
| 2007/0017527 A1 | 1/2007 | Totz | |
| 2007/0021737 A1 | 1/2007 | Lee | |
| 2007/0074720 A1 * | 4/2007 | Schwartz | A61B 1/267 128/200.26 |
| 2008/0058599 A1 * | 3/2008 | Schwartz | A61M 16/0488 600/139 |
| 2008/0200761 A1 * | 8/2008 | Schwartz | A61B 1/267 600/120 |
| 2008/0208000 A1 * | 8/2008 | Schwartz | A61M 16/0488 600/120 |
| 2008/0214891 A1 * | 9/2008 | Slenker | A61B 1/00091 600/109 |
| 2008/0230056 A1 | 9/2008 | Boedeker | |
| 2008/0236575 A1 | 10/2008 | Chuda | |
| 2008/0249483 A1 * | 10/2008 | Slenker | A61B 1/0055 604/275 |
| 2008/0308098 A1 * | 12/2008 | Schwartz | A61M 16/0418 128/200.26 |
| 2009/0107509 A1 | 4/2009 | Sniadach | |
| 2010/0095969 A1 * | 4/2010 | Schwartz | A61M 25/0136 128/207.14 |
| 2010/0108060 A1 | 5/2010 | Pecherer et al. | |
| 2010/0256446 A1 * | 10/2010 | Raju | A61B 1/00091 600/114 |
| 2010/0298644 A1 | 11/2010 | Kleene | |
| 2011/0118550 A1 | 5/2011 | Tulley | |
| 2011/0120458 A1 * | 5/2011 | Schwartz | A61B 1/267 128/200.26 |
| 2011/0196204 A1 * | 8/2011 | Setty | A61M 16/0488 600/120 |
| 2012/0078050 A1 * | 3/2012 | Schwartz | A61B 1/267 600/120 |
| 2013/0211263 A1 | 8/2013 | Boedeker | |
| 2014/0200405 A1 * | 7/2014 | Atlas | A61B 1/2673 600/109 |
| 2014/0275772 A1 | 9/2014 | Chuda | |
| 2014/0275778 A1 | 9/2014 | Gunday et al. | |
| 2015/0099927 A1 | 4/2015 | Sadoughi | |
| 2015/0366445 A1 * | 12/2015 | Rutgers | A61B 1/267 600/120 |
| 2016/0287348 A1 | 10/2016 | Vayser et al. | |
| 2017/0135566 A1 | 5/2017 | Gerrans | |
| 2017/0246410 A1 | 8/2017 | Levitan | |
| 2017/0258550 A1 | 9/2017 | Vazales | |
| 2018/0228557 A1 | 8/2018 | Darisse et al. | |
| 2018/0318534 A1 * | 11/2018 | Desatnik | A61M 16/0418 |
| 2018/0326629 A1 | 11/2018 | Miller et al. | |
| 2019/0014980 A1 | 1/2019 | Herskovic | |
| 2019/0125177 A1 | 5/2019 | Sutherland | |
| 2019/0160268 A1 | 5/2019 | Ngo-Chu et al. | |
| 2019/0350439 A1 | 11/2019 | Perez-Lizano | |
| 2020/0054849 A1 * | 2/2020 | Venticinque | A61B 1/267 |

OTHER PUBLICATIONS

Awake Bronchoscopic Intubation, Module 1: The Bronchoscope, Toronto General Hospital Department of Anesthesia Perioperative Interactive Education. Accessed Sep. 25, 2016. <http://pie.med.utoronto.ca/BI/BI_content/BI_module.html.>.

* cited by examiner

FIG. 8A

INTUBATING ENDOSCOPIC DEVICE

CROSS-REFERENCE TO RELATED APPLICATIONS

This application claims the benefit under 35 U.S.C. § 119(e) to U.S. Provisional Application Ser. No. 62/400,340 titled "INTUBATING ENDOSCOPIC DEVICE," filed Sep. 27, 2016, which is incorporated by reference herein in its entirety for all purposes.

FIELD OF THE DISCLOSURE

The present disclosure is related to an intubating device. The present disclosure is particularly related to an intubating device for assisting in introducing an endotracheal tube into an airway of a patient.

SUMMARY OF THE DISCLOSURE

In one aspect of the present disclosure, an intubating device is provided for use with an endotracheal tube. The intubating device includes a sheath having a distal end and a proximal end, the sheath being configured to be introduced into a body cavity, the sheath having a rigid section, and the sheath having a flexible section at the distal end, the flexible section being selectively bendable; and a control housing at the proximal end, the control housing comprising a deflector for selectively bending the flexible section of the sheath.

In some embodiments, the sheath extends along any or all of a light source channel, an imaging channel, and a gas channel.

In some embodiments, the sheath is configured and dimensioned to be received within an endotracheal tube having an inner diameter of at least 6 mm.

In some embodiments, the rigid section is between 30 centimeters and 32 centimeters in length, and the flexible section is between 3 centimeters and 5 centimeters in length.

In some embodiments, the rigid section comprises a curved portion towards the distal end adjacent to the flexible section.

In some embodiments, the rigid section has a centerline along its length that is nonlinear.

In some embodiments, any or all of the imaging channel, the gas channel, and the light source channel terminate at the distal end of the sheath.

In some embodiments, the imaging channel is configured to be connected to an optical viewer.

In some embodiments, the gas channel is configured to be connected to at least one of a gas source and a suction source.

In some embodiments, the device includes a tube stop configured to secure a first end of an endotracheal tube to the intubating device.

In some embodiments, the device includes a fluid (saline) channel.

In some embodiments, the device includes at least one flexible wire extending along the length of the sheath and connected to the deflector.

Another aspect of the present disclosure is directed to an intubating device for use with an endotracheal tube, the intubating device including a sheath having a distal end and a proximal end, the sheath being configured to be introduced into a body cavity, the sheath having a rigid section, and the sheath having a flexible section at the distal end, the flexible section being selectively bendable; the sheath extending along a light source channel, an imaging channel, and a gas channel; a control housing at the proximal end; the control housing comprising a deflector for selectively bending the flexible section of the sheath; wherein the sheath is configured to be received within an endotracheal tube having an inner diameter of at least 6 mm; and wherein the rigid section is between 30 centimeters and 32 centimeters in length, and the flexible section is between 3 centimeters and 5 centimeters in length.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION OF THE DISCLOSURE

The present disclosure relates generally to an intubating endoscopic device. Particularly, in some embodiments the present disclosure relates to a bronchoscope having a rigid section along the majority of its length and a flexible section at its distal end.

When not performed properly, tracheal intubation can cause respiratory-related injuries. Maintaining a patient's airway is important for a patient undergoing any procedure, particularly when the patient is under general anesthesia. If an airway cannot be quickly established, prolonged hypoxia can result, risking damage to vital organs such as the heart and the brain.

Traditional laryngoscopes lift the mandible and the tongue anteriorly (upward), which not only widens the visual space but also helps to lift the epiglottis up to allow visualization of the vocal cords and visualization of where to place the endotracheal tube (ETT) alongside it. This procedure is associated with significant cervical spine motion.

Flexible fiberoptic scopes require two hands and do not lift the mandible and adjacent soft tissues, but instead 'snake around' structures until the airway is seen. Accessory devices or aids might include a special oral airway to maintain a mid-line position and guide the flexible scope around the tongue and into the pharynx (i.e. past the base of the tongue. Another 'aid' is to have a second person either pull the tongue forward or manually lift the mandible forward. This procedure is associated with significantly less or no cervical spine motion compared to traditional laryngoscopes.

Videolaryngoscopes are like traditional laryngoscopes, but use a visual scope at its tip (rather than the user's own eyes) and, while the user holds the videolaryngoscope with one hand, the endotracheal tube with a special rigid stylet is passed alongside the videolaryngoscope into the airway with the user's other hand. This may require less mandibular displacement (i.e. jaw lift or thrust) as the vocal cords are seen at the tip of the device. This procedure is associated with less cervical spine motion than traditional laryngoscopy.

Traditional laryngoscopes and videolaryngoscopes are not low profile devices, and require enough space to pass both the device and, alongside the device, the styletted laryngoscope.

Flexible fiberoptic scopes and the intubating endoscopic device of the present disclosure are lower profile devices that only require the one device (with ETT on it) passed into the patient's mouth, behind the tongue and then guided toward the airway.

The device of the present disclosure has a straight rigid portion and a distal flexible portion, such that the rigid portion allows the user to lift the tongue and soft tissues. The flexible portion at the tip allows the user to search for and steer toward the airway structure (such as the vocal cords). Like a flexible bronchoscope this procedure is associated with less or no cervical spine motion compared to traditional laryngoscopy.

Embodiments of the device of the present disclosure are low profile, easy to handle scope that has the benefits of being rigid to allow easier handling using a single hand to place, and the ability to lift the tongue and mandible to expose the larynx, while having a flexible tip to allow search for and steering toward the vocal cords.

In contrast, a flexible fiberoptic scope requires two hands to guide the flexible fiberoptic scope.

Because a flexible fiberoptic scope is passed through the vocal cords into the distal part of the trachea to guide the ETT, this might cause trauma to the distal airway tissues. Unlike a flexible scope, the device of the present disclosure does not have to pass all the way into the airway or can even sit above the airway and guide (and allow a user to watch) the ETT pass into the trachea. Unlike laryngoscopes the device of the present disclosure can pass slightly into the airway to provide a more direct guide of the ETT. The device of the present disclosure can exhibit advantages of a flexible scope and a laryngoscope.

As discussed herein, the intubating device of the present disclosure includes a rigid section to allow for increased user accuracy in placement of an endotracheal tube, and also includes a flexible section to allow the placement of the endotracheal tube to adjust to the anatomy of a user's pharynx while minimizing potential blunt trauma injury to the airway structures.

Thus, some aspects and advantages of the intubating device of the present disclosure are that the intubating device can be grasped by one hand of a user during use. In particular, the intubating device can be held by a user in one hand to secure an airway, without the use of a second device, such as a laryngoscope blade.

Figure 1A:
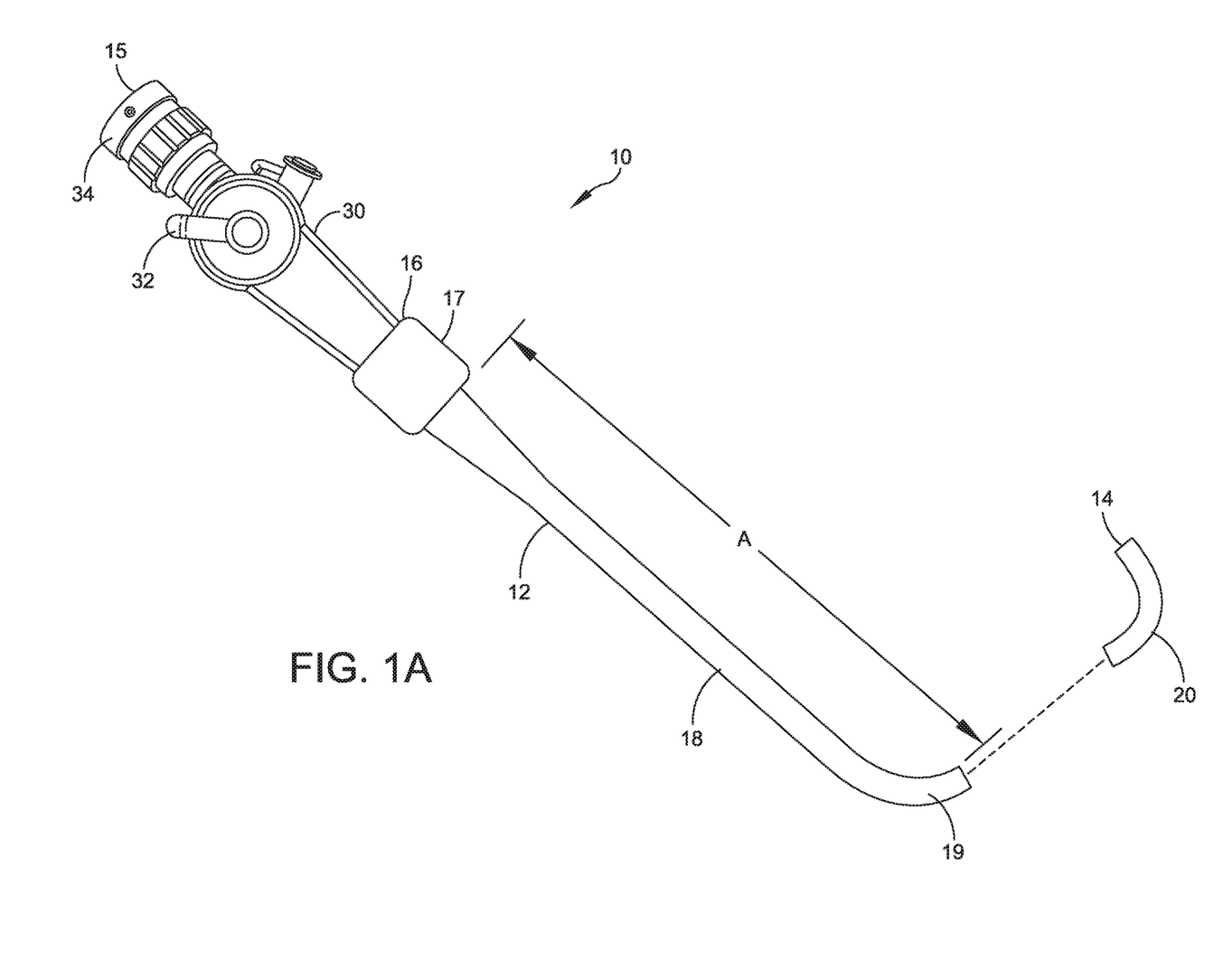
FIG. 1A shows a partially exploded view of a first embodiment of the intubating device of the present disclosure.

Other aspects and advantages of the intubating device of the present disclosure are, for example: it can conform to the configuration of the pharynx of a patient; it is portable; it is low profile (small, not long) easy to handle and to use and therefore provides for users to quickly become expert users of the intubating device; it is adjustable; it can be made inexpensively; it is generally straight or can be slightly bent, has a flexible and maneuverable tip, and is durable. FIG. 1A shows a first embodiment of an intubating device 10 of the present disclosure. The intubating device 10 includes a sheath 12 that has a distal end 14 and a proximal end 16, and is configured to be introduced into a body cavity, such as a mouth of a human patient. In some uses, the intubating device can be introduced at another point along an airway of a patient. The sheath 12 of FIG. 1A is shown in a partially exploded view, having a rigid section 18 and a flexible section 20 adjacent to the rigid section 18 and at the distal end 14 of the sheath 12. Although the sheath 12 of FIG. 1A is shown in a partially exploded view, the flexible section 20 is secured to the rigid section 18 when the intubating device 10 is in use, as shown in FIG. 1B.

The rigid section 18 may be reinforced by a rigid layer, such as a metal layer. The metal layer can be a strip along the length of the rigid section 18. In some embodiments, the metal layer is a strip that extends along the length of one or more sides of the rigid section 18. In some embodiments, the metal layer encircles the rigid section 18 and extends along the length of the rigid section 18.

Figure 1B:
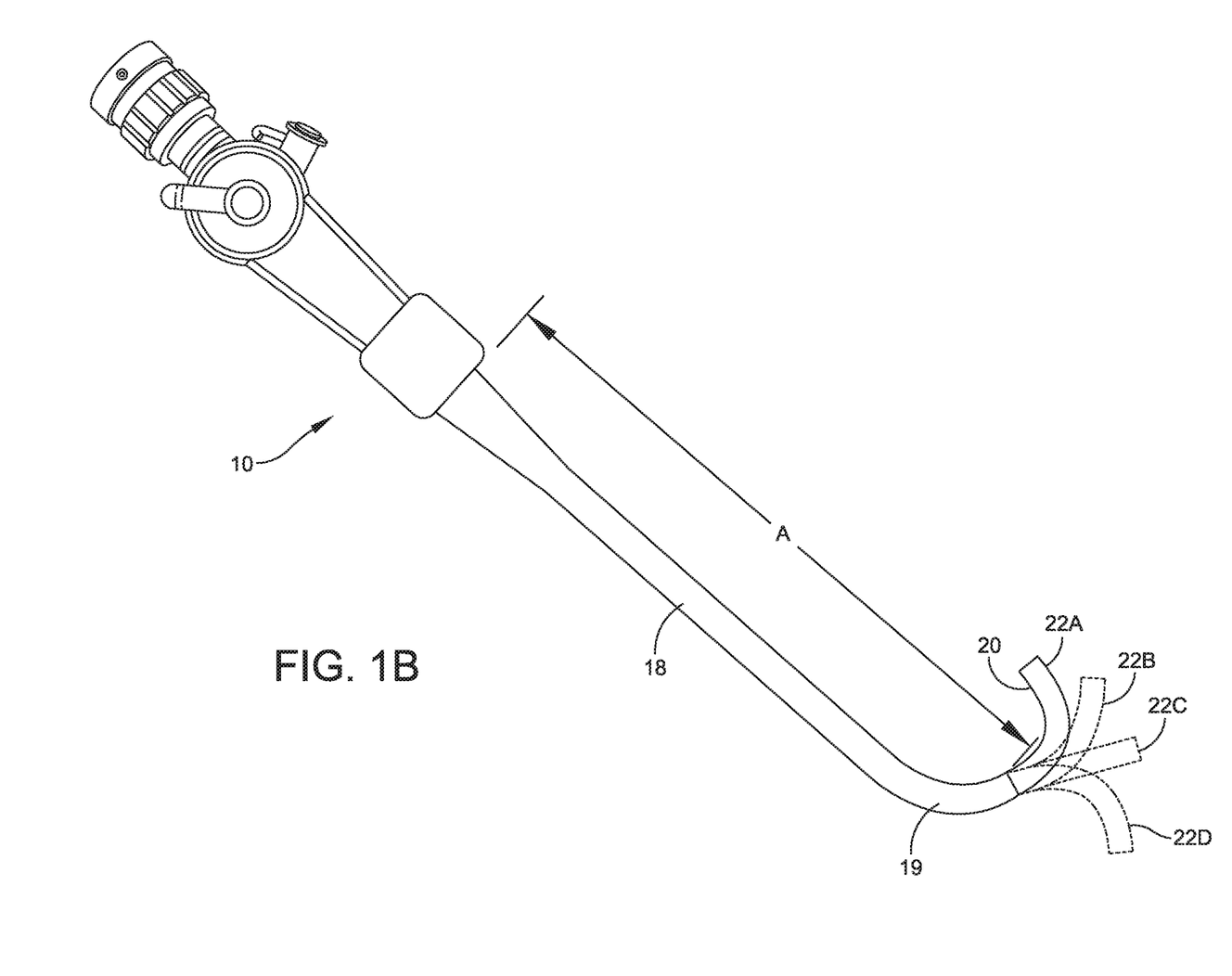
FIG. 1B shows the flexible portion of the device of FIG. 1A at various curvatures.

The flexible section 20 is configured to be selectively bendable, as shown in FIG. 1B, where the flexible section 20 has a curvature 22A that can be adjusted to various curvatures 22B, 22C, 22D of the flexible section 20 (as shown in broken lines for illustration purposes in FIG. 1B). With this arrangement, a user can adjust the curvature of the flexible section 20 of the sheath to navigate a body cavity, such as an airway of a patient.

Generally, the sheath is configured to be inserted into an airway. Generally, the sheath is configured to contain at least one light bundle in at least one light source channel and an image transmission bundle in an imaging channel. Each light bundle and each transmission bundle can be configured as a glass bundle. These glass bundles (the light bundle and the image transmission bundle) run the length of the endoscope containing thousands of glass fibers, which are for example approximately 8 microns to 10 microns in diameter. The image transmission bundle provides for light containing an image to travel along the length of the fiber, being internally reflected along its length to the eyepiece whilst still retaining a sharp image of the object. Because many of these glass fibers are bundled together, the image is built as a composite of that obtained by each fiber, similar to pixels on a television screen or another display. In some embodiments, a typical fiber optic bundle contains 10,000 glass fibers.

Figure 2:
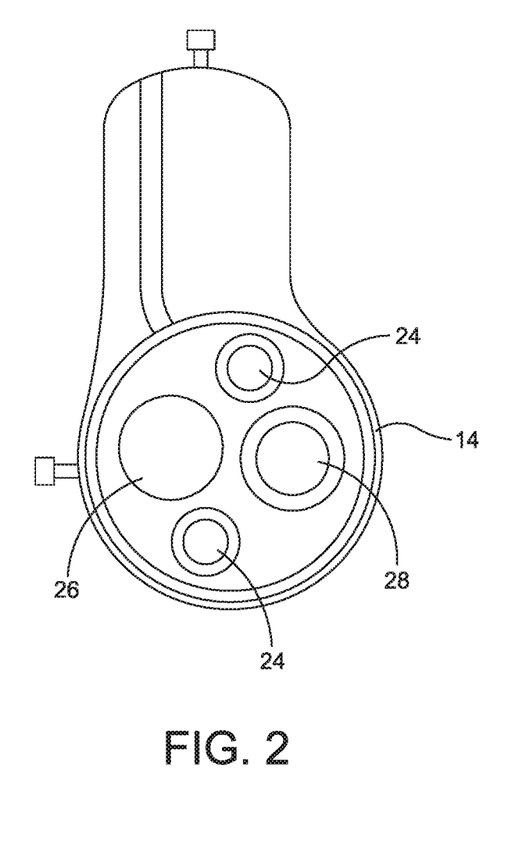
FIG. 2 shows a view of the distal end thereof.

In the embodiment of FIG. 1A, the sheath 12 surrounds a light source channel 24, an imaging channel 26, and a gas channel 28, as shown in the end view of FIG. 2. A light source port is disposed at the end of the light source channel 24, and a light bundle extends within the light source channel 24. A fiber optic port is disposed at the end of the imaging channel 26, and an image transmission bundle extends within the imaging channel 26. The imaging channel 26 may be a fiber optic guide channel or a channel for another imaging medium.

Some embodiments can include two light source channels 24 as shown in FIG. 2. Each light source channel is useful for transmitting light from a light source and providing light to a patient's airway at the distal end 14 of the sheath 12. The light source for a video bronchoscope is generally halogen or incandescent, and is transmitted via fiberoptic bundles. It is appreciated that the light source may also be LED or any other light source that is customary. The light source can be a portable battery powered source or connected via a cable.

Thus aspects and advantages of the intubating device of the present disclosure include that it can be used to provide a bright light source to a patient without risking heat injury to the patient. For example, in some embodiments, the light source can be remote from the distal end of the intubating device, so there is no risk of heat injury to the patient due to the light source.

The sheath also encloses a working channel (such as a gas channel) 28, which is provided for suction, instillation of local anesthetic, and oxygen delivery to the patient's airway. The sheath is configured with an oxygen port insufflation/suction port as shown at an end of the gas channel 28.

In some embodiments, an additional biopsy/suction channel can also be provided. Such a channel can be useful for applying suction to the patient's airway at the distal end of the sheath to collect liquids and/or solids within the airway, and can be provided separately from a gas channel for providing oxygen.

In some embodiments, a fluid channel is provided. For example, in some embodiments, a fluid channel is useful for introducing fluid to the patient's airway adjacent to the distal end of the sheath. In some embodiments, the fluid channel can be used to provide saline or a fluid that includes saline. In some embodiments, the fluid channel runs the length of the endoscope.

In some embodiments, the fluid channel, the biopsy/suction channel, and/or the second light source channel 24 can be enclosed within the sheath.

In the embodiment of the intubating device 10 of FIG. 1A, the sheath 12 encloses at least one light source channel 24, the imaging channel 26, and the gas channel 28 extending along the length rigid section and flexible section of the sheath. In the embodiment of the intubating device 10 of FIG. 1A, the imaging channel 26, the gas channel 28, and the light source channels 24 terminate at the distal end 14 of the sheath 12.

The intubating device 10 allows the user to control the curvature of the flexible section 20 of the sheath 12 with a deflector 32. The sheath 12 also encloses at least one tip bending guide wire extending along its length (not illustrated). A control housing 30 is shown adjacent to the proximal end 16 of the sheath 12 in FIG. 1A. The control housing 30 includes the deflector 32 for selectively bending the flexible section 20 of the sheath 12. The operation of the tip bending guide wire(s) and the deflector 32 is discussed in further detail below in relation to FIGS. 7A-8D.

The sheath 12 of the intubating device 10 is dimensioned and configured to be received within an endotracheal tube having an inner diameter that is at least 6 millimeters, for example between 6 millimeters and 9 millimeters. For example, the outer diameter of the rigid section 18 and flexible section 20 of the sheath can be between 5 millimeters and 6 millimeters in some embodiments. In some embodiments, the outer diameter of the rigid section 18 and the flexible section 20 of the sheath is 5 millimeters. It is also appreciated that the outer diameter of the sheath can be any dimension that is useful in intubating an airway.

In one embodiment of the device, the rigid section 18 has a length A that is between 30 centimeters and 32 centimeters in length, and the flexible section 20 that is between 3 centimeters and 5 centimeters in length when straightened.

In one embodiment of the intubating device of the present disclosure, the total length of the endoscopic device is typically in the range of 500 millimeters to 650 millimeters in length. In some embodiments, the length is 600 millimeters in length. It is appreciated that the length of the endoscopic device can be dimensioned to suit the needs of a patient having a longer or shorter airway without departing from the scope of the present invention.

Figure 3A:
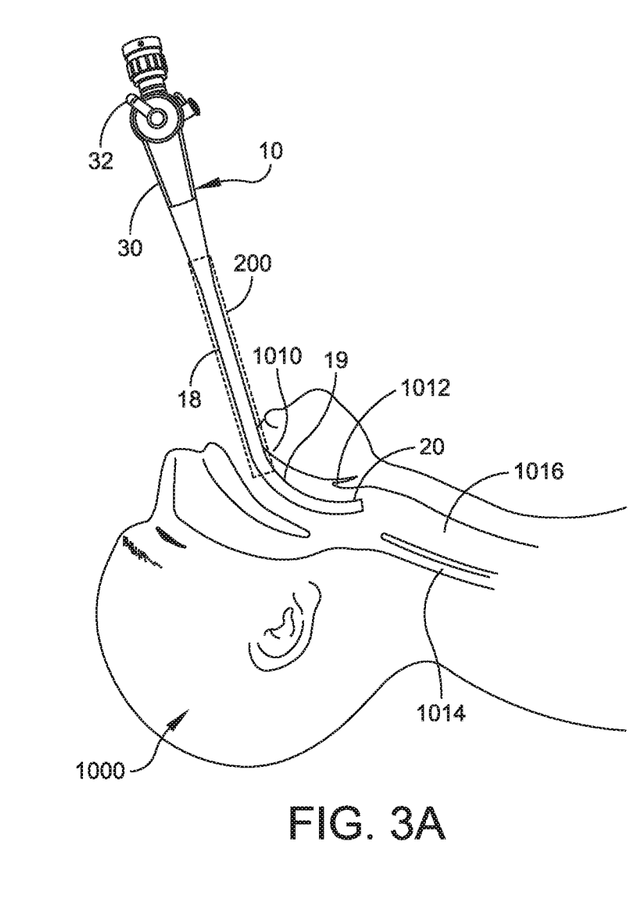
FIG. 3A shows the embodiment of FIG. 1A being inserted into an airway.
Figure 3B:
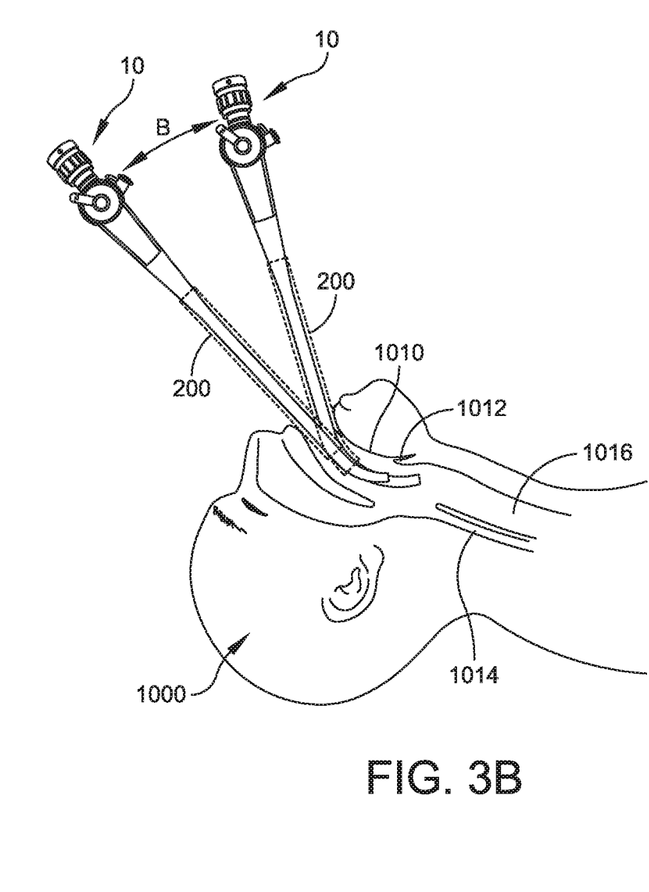
FIG. 3B shows how the position of the embodiment of FIG. 1A can be adjusted as it is inserted into an airway.

In one embodiment of the device, the rigid section 18 includes a curved portion 19. This curved portion 19 is adjacent to the flexible portion 20 of the sheath 12. This curved portion 19 is useful for lifting the tongue of the patient to open the airway when the patient is lying on his or her back. The curved portion 19 can engage the tongue of the patient so it can be lifted off of the posterior oropharynx, allowing better airway access. FIGS. 3A and 3B show an example of the orientation of the curved portion 19 in the sagittal plane view of a patient 1000. FIG. 3A shows a sagittal view of a patient 1000, showing the anatomical features such as the patient's tongue 1010, epiglottis 1012, esophagus 1014, and trachea 1016. FIGS. 3A and 3B show how the intubating device 10 can be rotated to along arrow B to different positions with respect to the patient 1000, while the flexible tip 20 remains in a position conducive to guiding an endotracheal tube 200 into position to maintain a patent airway. The endotracheal tube 200 is shown in broken lines in FIGS. 3A and 3B. It should be understood that FIG. 3B shows two positions of a single intubating device 10 for illustration purposes only. Only one intubating device 10 is needed at a given time. With this arrangement, the rigid section can be used to provide some lifting of the tongue and soft tissues. In addition, with this arrangement, the flexible tip provides for searching and steering toward of the patient airway (and vocal cords). With this arrangement, an airway can be intubated using the intubating device 10 without using a separate laryngoscope blade.

In one embodiment of the device, the rigid section of the sheath provides a mechanical advantage to the user when moving a patient's tongue out of the way to access an airway, while the flexible section allows the user to guide an endotracheal tube supported on the intubating device past the epiglottis and vocal cords of the patient with minimal or no injury to the patient. Because of the relative lengths of the rigid section and the flexible section of the sheath, the intubating device can be used without a laryngoscope blade, so there is decreased risk of excessive force applied by the operator of the intubating device to the patient's lower jaw and teeth. Because there is no need for a laryngoscope blade during insertion, the intubating device can be used with a single hand, enabling the second hand of the operator to be used for additional control if needed Another aspect and advantage of the intubating device is unlike some of the prior art devices which require a flexible fiberoptic scope to passed through the vocal cords of a patient in to the distal part of the trachea to guide an ETT, which might cause trauma to the distal airway tissues, the proposed device does not have to be passed all the way into the airway of a patient. It can be passed slightly into the airway of the patient to provide a more direct guide. Alternatively, it can be disposed above the airway of a patient and guide (and watch) the ETT into the trachea.

FIG. 1A shows an endotracheal tube stop (endotracheal tube holder) 17 at the proximal end 16 of the sheath. The endotracheal tube stop 17 can be used to releasably secure, such as by friction, an endotracheal tube 200, or another airway securing device, to the sheath 12 of the intubating device. This allows a user to insert the intubating device and tube 10 into the body cavity of the user and then release the endotracheal tube 200 from the intubating device when the user is ready. When the endotracheal tube 200 is released from the intubating device 10, the intubating device 10 may be withdrawn from the endotracheal tube 200, leaving the endotracheal tube 200 in place in the airway of the patient.

In some embodiments, the endotracheal tube stop 17 is configured to frictionally secure a first end of the endotracheal tube 200 to the intubating device at the first end.

In the embodiment of FIG. 1A, the distal end 14 of the sheath 12 has a blunt tip, to avoid injury to the patient's anatomy as the intubating device is inserted into the body cavity of the patient. It is appreciated that other tips such a rounded, curved, or other shapes as is customary can be used.

In some embodiments of the intubating device, the imaging channel 26 is connected to an optical viewer, such as an eyepiece 34 or a display. FIG. 1A shows an eyepiece 34 located at a proximal end 15 of the endoscopic intubating device 10 on the control housing 30, so that a user can look through the eyepiece 34 to see the anatomy of the airway and to visually confirm placement of the endotracheal tube 200, or another airway securing device. The eyepiece 34 is preferably a high resolution eyepiece for conclusive placement of an endotracheal tube 200 within an airway of a patient. A diopter ring (not labeled) is provided for focusing.

Alternatively, the eyepiece 34 can be attached to a camera for display on a screen. Some fiberoptic embodiments of the device can have an eye piece. Some video scope embodiments of the device according to the present disclosure do not.

In some embodiments, the gas channel 28 is configured to be connected to at least one of a gas source and a suction source. Thus, the gas channel 28 can be used to provide gas to the body cavity when the gas channel 28 is connected to a gas source, and can be used to remove air, gas, or solids from the body cavity when the gas channel 28 is connected to a suction source.

Figure 4A:
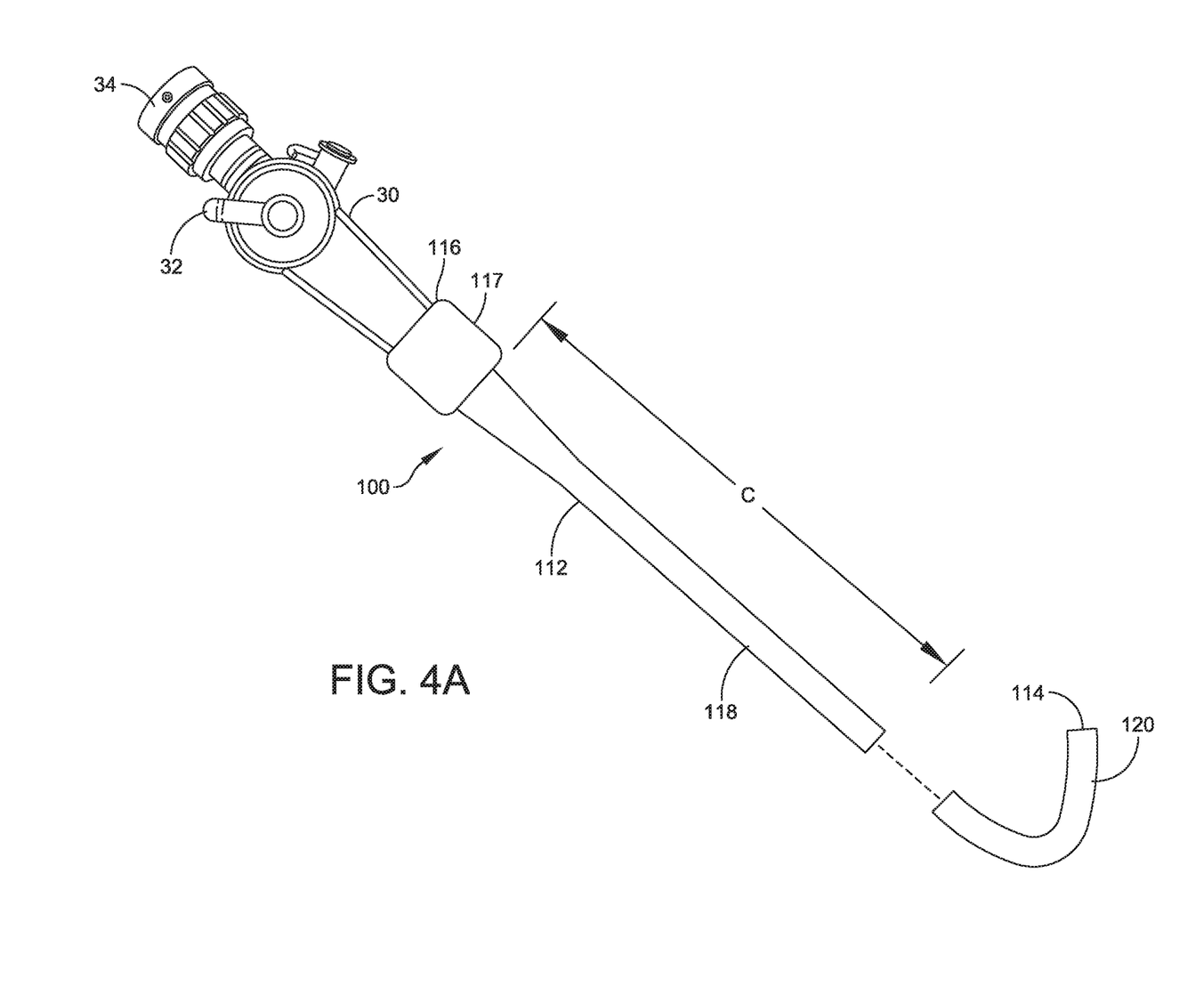
FIG. 4A shows a partially exploded view of a second embodiment of the intubating device of the present disclosure.

Turning to FIG. 4A, the embodiment of the endoscopic intubating device 100 of FIG. 4A is similar to the embodiment 10 of FIG. 1A, except the rigid section 118 of the sheath 112 does not include a curved portion towards the distal end 114 of the sheath 112. This embodiment is generally straight with a maneuverable portion 120.

The curvature of the rigid section is generally not adjustable within the body cavity of a patient or by use of the deflector 32.

Figure 4B:
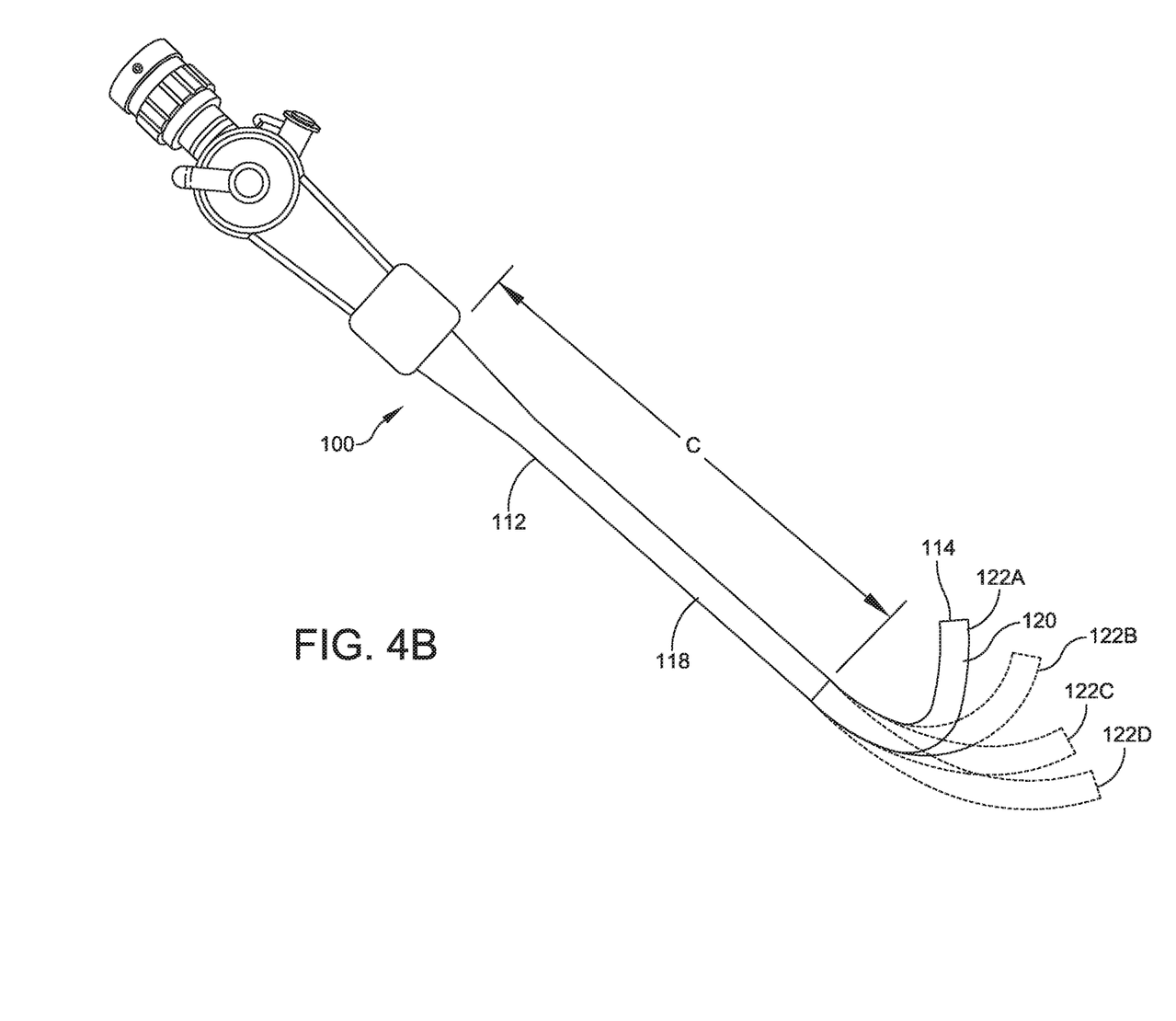
FIG. 4B shows the flexible portion of the device of FIG. 4A at various curvatures.

FIG. 4A shows an endotracheal tube stop (endotracheal tube holder) 117 at the proximal end 116 of the sheath. The endotracheal tube stop 117 can be used to releasably secure, such as by friction, an endotracheal tube 200, or another airway securing device, to the sheath 112 of the intubating device. This allows a user to insert the intubating device 100 into the body cavity of the user and then release the endotracheal tube 200 from the intubating device when the user is ready. When the endotracheal tube 200 is released from the intubating device 100, the intubating device 100 may be withdrawn from the endotracheal tube 200, leaving the endotracheal tube 200 in place in the airway of the patient. Like the intubating device 10, the intubating device 100 includes a flexible section 120 that is selectively bendable, as shown in FIG. 4B, where the flexible section 120 has a curvature 122A that can be adjusted, such as to various curvatures 122B, 122C, 122D as shown in broken lines for illustration purposes in FIG. 4A. A user can adjust the curvature of the flexible section 120 of the sheath to navigate a body cavity, such as an airway of a patient.

In the embodiment of FIG. 4A, the rigid section 118 has a length C that is between 30 centimeters and 32 centimeters in length, and the flexible section 120 is between 3 centimeters and 5 centimeters in length when straightened.

In the embodiment of the intubating device 100 of FIG. 4A, the distal end 114 of the sheath 112 has a blunt tip, to avoid injury to the patient's anatomy as the intubating device is inserted into the body cavity of the patient. It is appreciated that other tips such a rounded, curved, or other shapes as is customary can be used.

Figure 5:
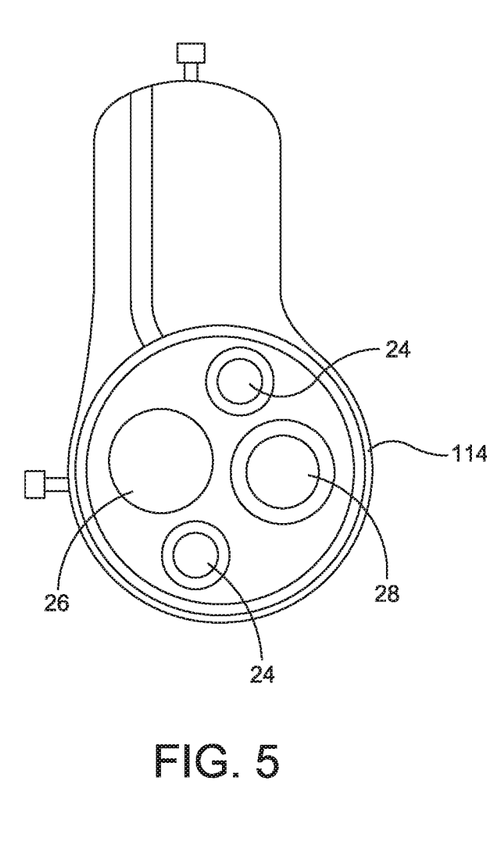
FIG. 5 shows a view of the distal end thereof.

FIG. 5 shows an end view of the sheath 112, which is similar to the end view of the embodiment of FIG. 2. For the sake of brevity, the description of FIG. 2 applies to FIG. 5 and will not be repeated here.

Figure 6:
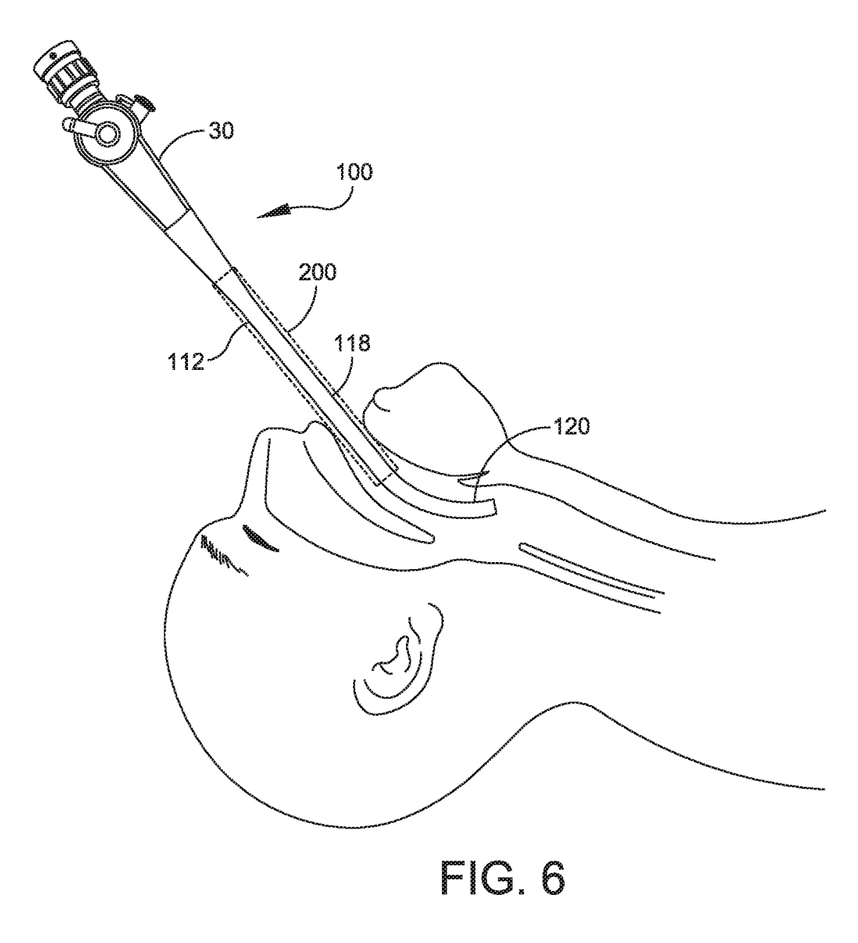
FIG. 6 shows the embodiment of FIG. 4A being inserted into an airway.

FIG. 6 shows the intubating device of FIG. 4A when it is being used to position the endotracheal tube 200 into the airway. For the sake of brevity, the descriptions of FIGS. 3A-3B apply to FIG. 6 and will not be repeated here.

Figure 7A:
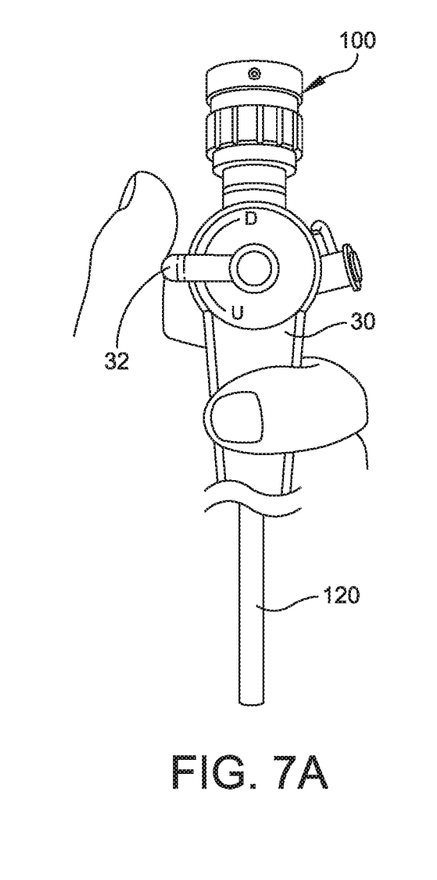
FIG. 7A shows the deflector in a first position.
Figure 7B:
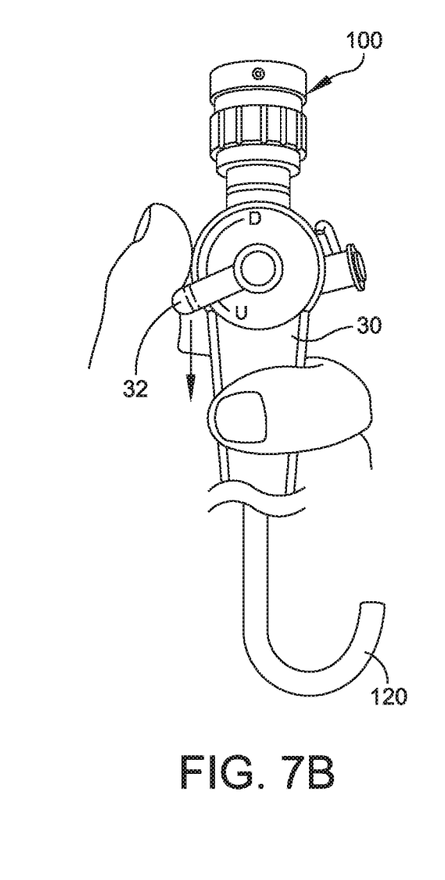
FIG. 7B shows the deflector in a second position.
Figure 7C:
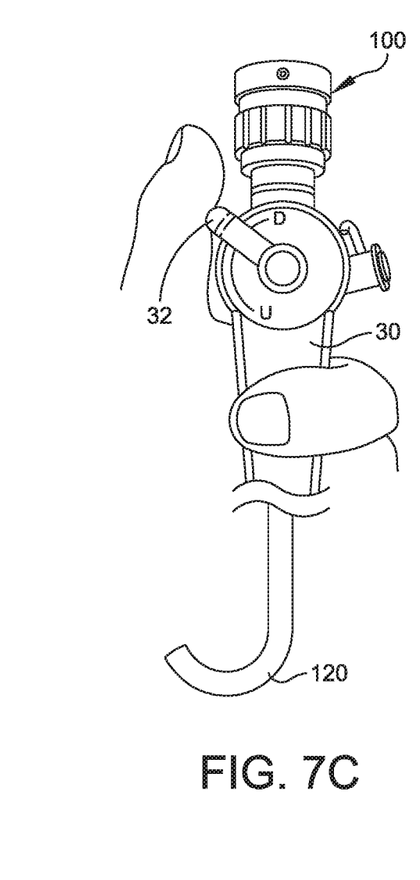
FIG. 7C shows the deflector in a third position.
Figure 8A:
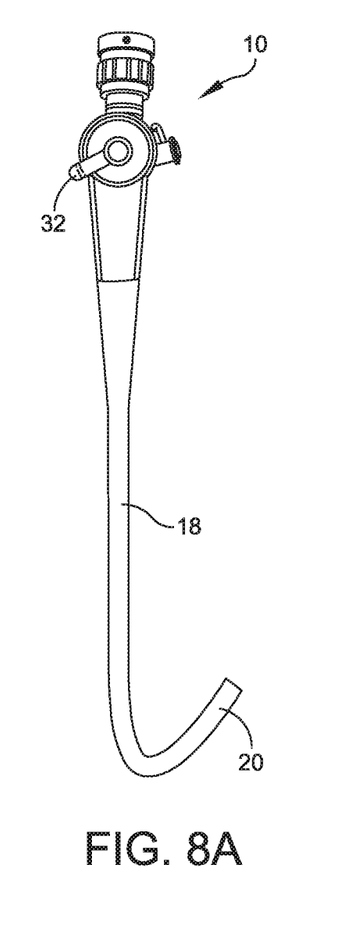
FIG. 8A shows the flexible section of a sheath bent to a first geometry.
Figure 8B:
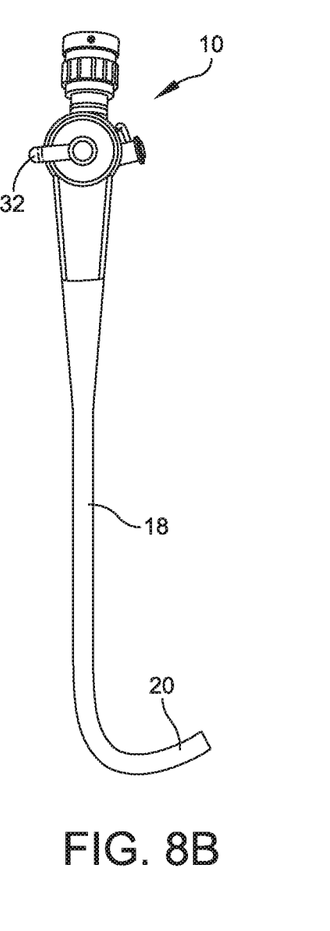
FIG. 8B shows the flexible section of a sheath bent to a second geometry.
Figure 8C:
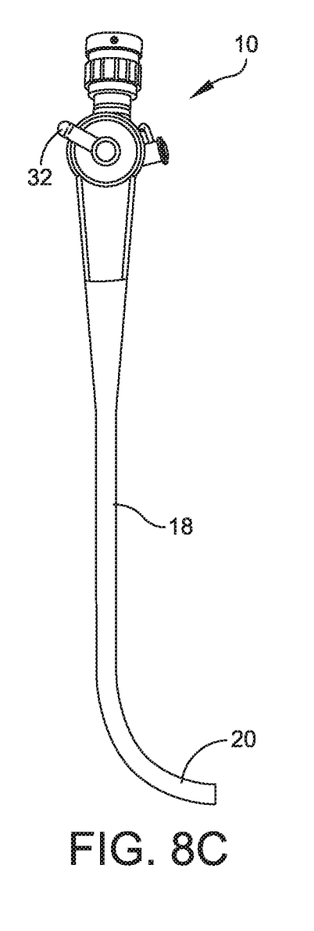
FIG. 8C shows the flexible section of a sheath bent to a third geometry.
Figure 8D:
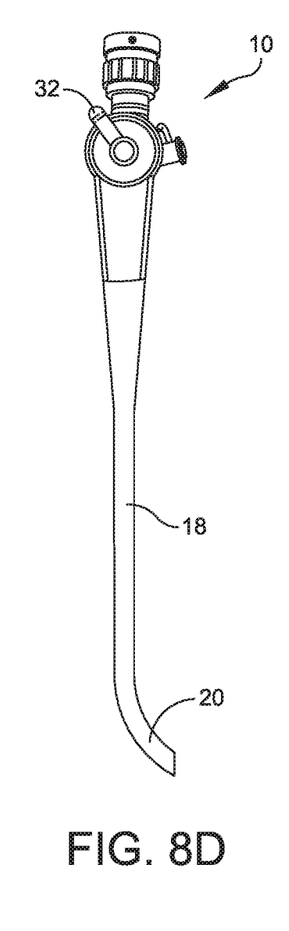
FIG. 8D shows the flexible section of a sheath bent to a fourth geometry.

FIGS. 7A-7C show various positions of the deflector (control lever) 32 that is rotatably secured to the control housing 30. In FIG. 7A, the deflector 32 is at a first position with respect to the housing 30, and the flexible section is straight. In FIG. 7B, the deflector 32 has been rotated counterclockwise from the first position to a second position with respect to the housing 30, and the flexible section 120 is flexed to the curvature shown. In FIG. 7C, the deflector 32 has been rotated clockwise from the first position to a third position with respect to the housing 30, and the flexible section 120 is extended. The deflector (or control lever) controls the flexible section at the distal end (tip) of the sheath. The deflector provides for movement of the flexible tip in a vertical plane, as shown in FIGS. 7A-7C.

In some embodiments, two wires extend from the handle of the device to the distal tip in the sheath. Rotating the deflector down changes the curvature of the flexible section to move the distal tip up and rotating the deflector up points the tip down. In some embodiments, side to side movement is accomplished by rotation of the body of the bronchoscope with the operator's wrist and shoulder. With this arrangement, each flexible guide wire is connected to the distal end of the sheath and is connected to the deflector (control lever). Rotation of the deflector 32 between the first position, the second position, and the third position of FIGS. 7A-7C causes the wire to be advanced or retracted in relation to the control housing 30, causing the respective curvatures of the flexible section 120 in FIGS. 7A-7C. Where two flexible wires are used, the deflector could cause a first wire to advance while causing a second wire to retract, with the first wire located at a first circumferential position along an inner perimeter of the sheath and with the second wire located at a diametrically opposed circumferential position along the inner perimeter of the sheath.

In some embodiments, each tip bending guide wire has a first end secured to the deflector 32 and movable by the deflector 32, and the guide wire has a second end secured to the distal end of the sheath. In some embodiments, rotation of the deflector 32 causes extension or retraction of each guide wire to effect a change in curvature of the flexible section. In some embodiments, each guide wire is contained within a guide wire channel extending through the rigid section 18 and the flexible section.

Other mechanisms can be used to cause the flexible section of the sheath to curve, without departing from the scope of the present disclosure.

FIGS. 8A-8D show some examples of how the flexible section 20 can by dynamically bent to adjust to anatomical features within a body cavity, such as an airway. In FIGS. 8A-8D, the flexible section 20 has different degrees of curvature to conform to the anatomy of an airway of a human patient or another patient.

It is also appreciated that the number and types of channels within the sheath 12, 112 can be changed without departing from the scope of the present disclosure.

It is also appreciated that the intubating device of the present disclosure may be used alone or in combination with other devices, such as laryngeal mask airway (LMA) devices.

It is also appreciated that the intubating device of the present disclosure is portable and reusable.

It is also appreciated that the intubating device of the present disclosure is easy to maintain and clean. For example, because there is no need for a laryngoscope blade, there is at least one less device to clean after use.

Embodiments are not limited in their application to the details of construction and the arrangement of components set forth in the following description or illustrated in the drawings. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment, it is to be appreciated various alterations, modifications, and improvements will readily occur to those skilled in the art. Such alterations, modifications, and improvements are intended to be part of this disclosure, and are intended to be within the scope of the disclosure. Accordingly, the foregoing description and drawings are by way of example only.

What is claimed is:

1. An intubating device for use with an endotracheal tube, the intubating device comprising:
    a sheath that is configured to be received within an endotracheal tube, the sheath having a distal end and a proximal end, the sheath being configured to be introduced into a body cavity, the sheath having a rigid section that provides a mechanical advantage to a user when lifting the patient's tongue off of the posterior oropharynx and out of the way to access an airway of the patient, and the sheath having a flexible section at the distal end, the flexible section being selectively bendable; and
    a control housing at the proximal end,
    the control housing comprising a deflector for selectively bending the flexible section of the sheath to allow the user to guide the endotracheal tube past the patient's epiglottis and vocal cords,
    wherein the rigid section comprises a straight portion and a curved portion, the straight portion extending from the proximal end to the curved portion that is located at a distal end of the rigid section adjacent to the flexible section,
    wherein the flexible section has an outer diameter that is substantially the same as an outer diameter of the curved portion of the rigid section, and
    wherein the intubating device is configured for single-handed use with the endotracheal tube to secure an airway.

2. The intubating device of claim 1, wherein the sheath is configured to be received within an endotracheal tube having an inner diameter of at least 6 mm.

3. The intubating device of claim 1, wherein the rigid section is between 30 centimeters and 32 centimeters in length, and the flexible section is between 3 centimeters and 5 centimeters in length.

4. The intubating device of claim 1, further comprising any or all of a light source channel, an imaging channel, and a gas channel enclosed by the sheath.

5. The intubating device of claim 4, wherein the imaging channel, the gas channel, and the light source channel terminate at the distal end of the sheath.

6. The intubating device of claim 4, wherein the imaging channel is configured to be connected to an optical viewer.

7. The intubating device of claim 4, wherein the gas channel is configured to be connected to at least one of a gas source and a suction source.

8. The intubating device of claim 4, further comprising a fluid channel.

9. The intubating device of claim 1, further comprising a tube stop configured to secure a first end of an endotracheal tube to the intubating device.

10. The intubating device of claim 1, further comprising at least one flexible wire extending along the length of the sheath connected to the deflector and to the flexible section.

11. The intubating device of claim 10, wherein the at least one flexible wire comprises two wires.

12. The intubating device of claim 1, wherein the intubating device is an oral intubating device, and wherein the curved portion is configured for lifting the patient's tongue to open the airway of the patient when the patient is lying on his or her back.

13. An intubating device for use with an endotracheal tube, the intubating device comprising:
    a sheath having a distal end and a proximal end, the sheath being configured to be introduced into a body cavity, the sheath having a rigid section, and the sheath having a flexible section at the distal end, the flexible section being selectively bendable, the rigid section comprising a straight portion and a curved portion, the straight portion extending from the proximal end to the curved portion that is located at a distal end of the rigid section adjacent to the flexible section;
    the sheath extending along a light source channel, an imaging channel, and a gas channel; and
    a control housing at the proximal end,
    the control housing comprising a deflector for selectively bending the flexible section of the sheath,
    wherein the sheath is configured to be received within an endotracheal tube having an inner diameter of at least 6 mm,
    wherein the rigid section is between 30 centimeters and 32 centimeters in length, and the flexible section is between 3 centimeters and 5 centimeters in length, and
    wherein the flexible section has an outer diameter that is substantially the same as an outer diameter of the curved portion of the rigid section.

14. An intubating device for use with an endotracheal tube for intubating a patient, the intubating device comprising:
    a sheath that is configured to be received within an endotracheal tube, the sheath having a distal end and a proximal end, the sheath being configured to be introduced into a body cavity, the sheath having a rigid section that provides a mechanical advantage to a user when lifting the patient's tongue off of the posterior oropharynx and out of the way to access an airway of the patient, and the sheath having a flexible section at the distal end, the flexible section being selectively bendable;

a control housing at the proximal end; and a deflector rotatably secured to the control housing for selectively bending the flexible section of the sheath to allow the user to guide the endotracheal tube past the patient's epiglottis and vocal cords, wherein the rigid section comprises a straight portion and a curved portion, the straight portion extending from the proximal end to the curved portion that is located at a distal end of the rigid section adjacent to the flexible section, wherein the flexible section has an outer diameter that is substantially the same as an outer diameter of the curved portion of the rigid section, and wherein the intubating device is a single-piece intubating device configured for use with the endotracheal tube for intubating a patient without using a laryngoscope blade.

15. The intubating device of claim 14, wherein the intubating device is an oral intubating device, and wherein the curved portion is configured for lifting the patient's tongue to open the airway of the patient when the patient is lying on his or her back.

16. The intubating device of claim 14, further comprising any or all of a light source channel, an imaging channel, and a gas channel enclosed by the sheath.

17. The intubating device of claim 16, wherein the imaging channel, the gas channel, and the light source channel terminate at the distal end of the sheath.

18. The intubating device of claim 16, wherein the imaging channel is configured to be connected to an optical viewer.

19. The intubating device of claim 14, further comprising a tube stop configured to secure a first end of an endotracheal tube to the intubating device.

20. The intubating device of claim 14, further comprising at least one flexible wire extending along the length of the sheath connected to the deflector and to the flexible section.

* * * * *